(12) United States Patent
Kyritsis

(10) Patent No.: US 7,866,468 B2
(45) Date of Patent: Jan. 11, 2011

(54) MEDICAL INSTRUMENT STERILIZATION POUCH

(76) Inventor: George Kyritsis, 3086 Dagenais Boulevard West, Fabreville QB (CA) H7P 1T6

( * ) Notice: Subject to any disclaimer, the term of this patent is extended or adjusted under 35 U.S.C. 154(b) by 895 days.

(21) Appl. No.: 11/622,942

(22) Filed: Jan. 12, 2007

(65) Prior Publication Data
US 2008/0171161 A1 Jul. 17, 2008

(51) Int. Cl.
*B65D 83/10* (2006.01)
(52) U.S. Cl. .................................. 206/363; 206/484.1
(58) Field of Classification Search ............. 206/484.1, 206/484, 484.2, 438, 439, 363, 364, 365; 493/186, 189, 199, 227
See application file for complete search history.

(56) References Cited

U.S. PATENT DOCUMENTS

| | | | |
|---|---|---|---|
| 4,358,015 A * | 11/1982 | Hirsch | 206/439 |
| 4,480,751 A | 11/1984 | Lueptow | |
| 4,660,721 A | 4/1987 | Mykleby | |
| 4,903,718 A | 2/1990 | Sullivan | |
| 5,344,017 A | 9/1994 | Wittrock | |
| 5,490,596 A | 2/1996 | Katz | |
| 5,655,653 A | 8/1997 | Chester | |
| 5,836,444 A | 11/1998 | Hoevel et al. | |
| 6,251,489 B1 | 6/2001 | Weiss et al. | |
| 6,582,654 B1 | 6/2003 | Kral et al. | |
| 6,594,971 B1 * | 7/2003 | Addy et al. | 53/413 |
| 6,767,509 B1 * | 7/2004 | Griesbach et al. | 422/29 |
| 7,074,362 B2 | 7/2006 | Walsh | |
| 2001/0023001 A1 * | 9/2001 | Weiss et al. | 428/35.2 |
| 2003/0185703 A1 | 10/2003 | Walsh | |
| 2005/0092636 A1 * | 5/2005 | Su-Syin | 206/363 |
| 2006/0240203 A1 * | 10/2006 | Matsumoto et al. | 428/35.2 |
| 2009/0188826 A1 * | 7/2009 | Porteous et al. | 206/459.5 |

FOREIGN PATENT DOCUMENTS

| | | |
|---|---|---|
| DE | 3712779 | 11/1988 |
| GB | 870180 | 6/1961 |
| JP | 08168518 | 7/1996 |

OTHER PUBLICATIONS

European Patent Office, European Search Report, Application/Patent No. 08386001.5-2310/1955669; Apr. 23, 2009, 9 pages.

* cited by examiner

*Primary Examiner*—Jacob K Ackun, Jr.
(74) *Attorney, Agent, or Firm*—Neustel Law Offices

(57) ABSTRACT

A medical instrument sterilization pouch for efficiently bagging hinged instruments. The medical instrument sterilization pouch generally includes a pouch including a first layer and a second layer, wherein the first layer and/or the second layer are comprised of a gas permeable material and wherein the first layer is attached to the second layer via an outer seal substantially surrounding an outer perimeter of the first layer and the second layer. The first layer and the second layer are further impermeable to micro-organisms or toxins. The pouch includes a first lower portion and a second lower portion, wherein the first lower portion is separated from the second lower portion and wherein the first lower portion and the second lower portion form a recessed portion between thereof. The pouch preferably receives a medical instrument (i.e. surgical pliers), wherein the medical instrument is sterilized within the pouch and is then positioned upon a respective tool rack (i.e. pliers rack).

6 Claims, 17 Drawing Sheets

MEDICAL INSTRUMENT STERILIZATION POUCH

CROSS REFERENCE TO RELATED APPLICATIONS

Not applicable to this application.

STATEMENT REGARDING FEDERALLY SPONSORED RESEARCH OR DEVELOPMENT

Not applicable to this application.

BACKGROUND OF THE INVENTION

1. Field of the Invention

The present invention relates generally to sterilization pouches and more specifically it relates to a medical instrument sterilization pouch for efficiently bagging hinged instruments.

2. Description of the Related Art

Any discussion of the prior art throughout the specification should in no way be considered as an admission that such prior art is widely known or forms part of common general knowledge in the field.

Sterilization pouches have been in use for years. Typically, when in a medical, dental or other similar environment it is necessary to keep all the instruments in pouches prior to use. The pouches effectively serve to prevent germs or other harmful toxins from coming in contact with the instruments when the instruments are not being used. The instruments are also generally sterilized prior to being inserted into the pouch or sterilized while inserted within the pouch.

Sterilization pouches are manufactured from many different materials, sizes and with many different sealing mechanisms. Although, one universal feature that generally exists in all sterilization pouches is that the sterilization pouches are generally rectangular in shape. This poses a problem with respect to hinged instruments, such as but not limited to orthodontic pliers and surgical pliers in that the hinged instruments can not adequately fit on their respective tool racks (i.e. pliers rack) once the hinged instruments are in the pouch. Because of the general lack of efficiency and practicality in the prior art there is the need for a new and improved medical instrument sterilization pouch for efficiently bagging hinged instruments.

BRIEF SUMMARY OF THE INVENTION

The general purpose of the present invention is to provide a medical instrument sterilization pouch that has many of the advantages of the sterilization pouches mentioned heretofore. The invention generally relates to a sterilization pouch which includes a pouch including a first layer and a second layer, wherein the first layer and/or the second layer are comprised of a gas permeable material and wherein the first layer is attached to the second layer via an outer seal substantially surrounding an outer perimeter of the first layer and the second layer. The first layer and the second layer are further impermeable to micro-organisms or toxins. The pouch includes a first lower portion and a second lower portion, wherein the first lower portion is separated from the second lower portion and wherein the first lower portion and the second lower portion form a recessed portion between thereof. The pouch preferably receives a medical instrument (i.e. surgical pliers), wherein the medical instrument is sterilized within the pouch and is then positioned upon a respective tool rack (i.e. pliers rack).

There has thus been outlined, rather broadly, some of the features of the invention in order that the detailed description thereof may be better understood, and in order that the present contribution to the art may be better appreciated. There are additional features of the invention that will be described hereinafter and that will form the subject matter of the claims appended hereto.

In this respect, before explaining at least one embodiment of the invention in detail, it is to be understood that the invention is not limited in its application to the details of construction or to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

An object is to provide a medical instrument sterilization pouch for efficiently bagging hinged instruments.

Another object is to provide a medical instrument sterilization pouch that accommodates a variety of different style hinged instruments.

An additional object is to provide a medical instrument sterilization pouch that may be utilized with non-hinged instruments.

A further object is to provide a medical instrument sterilization pouch that allows the hinged instruments to be placed on their respective holding racks (i.e. pliers rack) after the hinged instruments are bagged.

Another object is to provide a medical instrument sterilization pouch that includes a durable outer material to prevent puncture by the instrument.

Another object is to provide a medical instrument sterilization pouch that mimics the shape and size of the medical instruments utilized thus producing less environmental and biological waste.

Other objects and advantages of the present invention will become obvious to the reader and it is intended that these objects and advantages are within the scope of the present invention. To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWINGS

Various other objects, features and attendant advantages of the present invention will become fully appreciated as the same becomes better understood when considered in conjunction with the accompanying drawings, in which like reference characters designate the same or similar parts throughout the several views, and wherein.

DETAILED DESCRIPTION OF THE INVENTION

A. Overview

Figure 1:
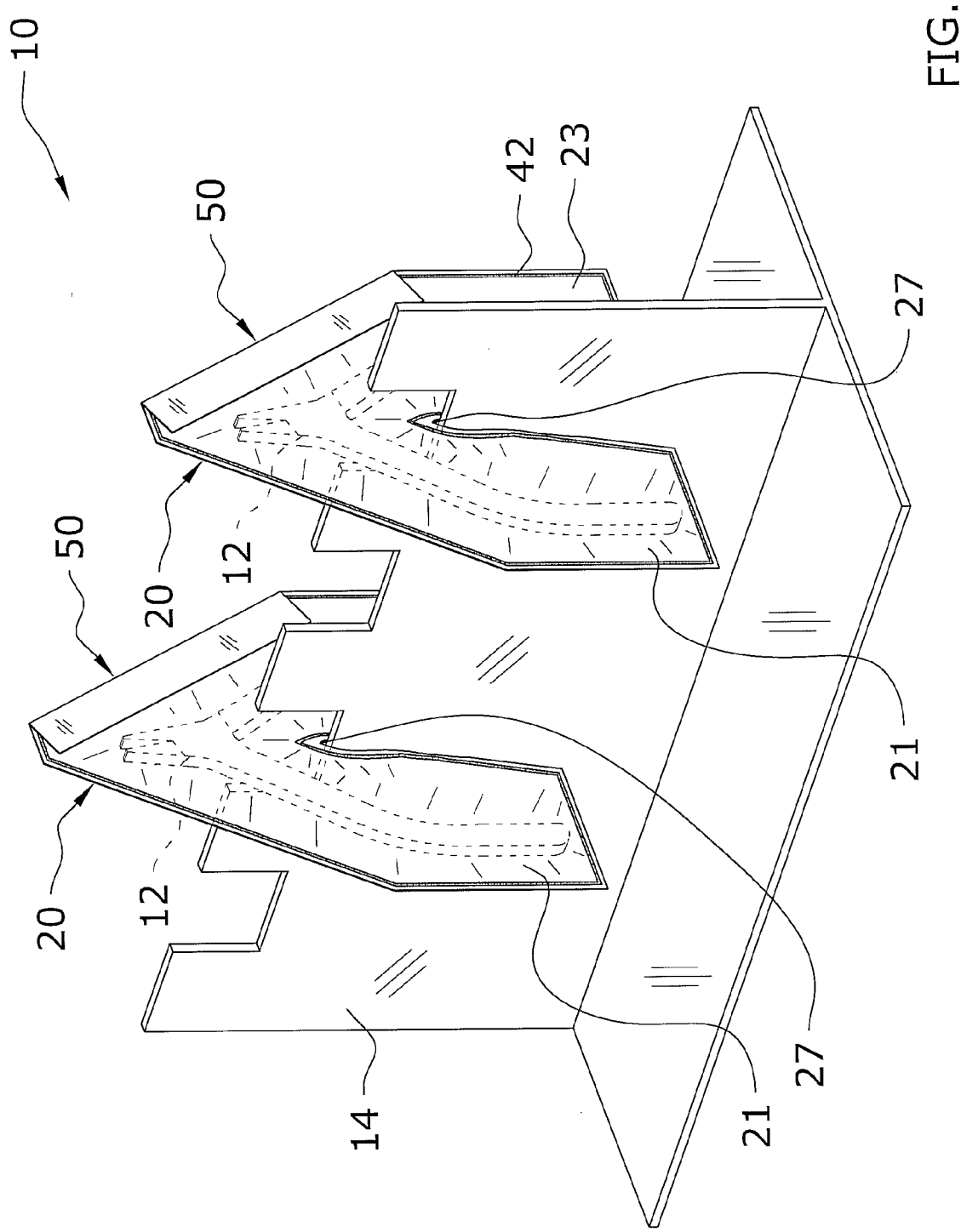
FIG. 1 is an upper perspective view of the present invention in use and positioned upon a tool rack.

Turning now descriptively to the drawings, in which similar reference characters denote similar elements throughout the several views, FIGS. 1 through 17 illustrate a medical instrument 12 sterilization pouch 10, which comprises a pouch 20 including a first layer 30 and a second layer 40, wherein the first layer 30 and/or the second layer 40 are comprised of a gas permeable material and wherein the first layer 30 is attached to the second layer 40 via an outer seal 42 substantially surrounding an outer perimeter of the first layer 30 and the second layer 40. The pouch 20 includes a first lower portion 21 and a second lower portion 23, wherein the first lower portion 21 is separated from the second lower portion 23 and wherein the first lower portion 21 and the second lower portion 23 form a recessed portion 27 between thereof. The pouch 20 preferably receives a medical instrument 12 (i.e. surgical pliers), wherein the medical instrument 12 is sterilized within the pouch 20 and is then positioned upon a respective tool rack 14 (i.e. pliers rack).

B. Pouch

The pouch 20 is preferably comprised of a configuration to hold hinged medical instruments 12, such as but not limited to orthodontic pliers, surgical pliers, tweezers and scissors. The pouch 20 also preferably adequately holds non-hinged medical instruments 12, such as but not limited to inspection mirrors, dental picks, dental scalers and spatulas, wherein the non-hinged medical instruments 12 are simply inserted into the pouch 20 in a crossed manner. It is also appreciated that the pouch 20 may hold various other tools or equipment not associated with medical use. The pouch 20 preferably mimics the shape of the medical instrument 12, thus requiring the minimal amount of packaging for each medical instrument 12.

Figure 6:
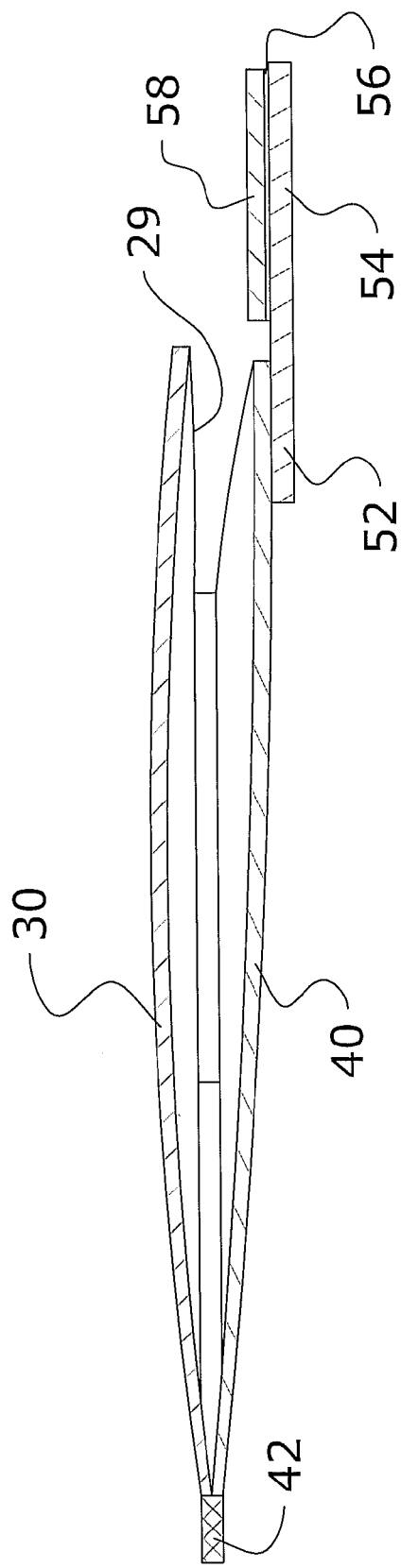
FIG. 6 is a sectional view taken along lines 6-6 of FIG. 2.

The pouch 20 includes a first layer 30 and a second layer 40 as shown in FIG. 6. The first layer 30 and the second layer 40 are preferably both comprised of a gas permeable material. The first layer 30 and the second layer 40 are further impermeable to micro-organisms or toxins. The first layer 30 and the second layer 40 are further preferably comprised of a material resistant enough to withstand both steam and dry heat sterilization cycles. The first layer 30 and the second layer 40 may further be comprised of various materials, such as but not limited to nylon films, polypropylene films, polyethylene films, polyester polypropylene pellicles, blends of medical grade paper or a combination of two or more materials. The first layer 30 and the second layer 40 are further preferably comprised of a transparent material so as to easily view the medical instrument 12 within the pouch 20. The first layer 30 and the second layer 40 may also include chemical, steam and heat activated indicators. The indicators are preferably painted on the first layer 30 or the second layer 40.

The first layer 30 and the second layer 40 may be comprised of a plurality of different shapes and sizes, wherein each of the configurations of the first layer 30 and the second layer 40 forms a recessed portion 27 to receive the legs of a medical instrument 12 as illustrated in FIGS. 1 through 17. The first layer 30 and the second layer 40 are further preferably comprised of substantially similar configurations.

The first layer 30 and the second layer 40 are preferably attached substantially near an outer perimeter of the first layer 30 and the second layer 40 via an outer seal 42 as shown in FIGS. 1 through 5. The outer seal 42 extends substantially across an entire perimeter of the first layer 30 and the second layer 40, wherein the outer seal 42 leaves room for an opening 29 along at least one outer edge to access the interior between the first layer 30 and the second layer 40.

The pouch 20 includes a first lower portion 21, a second lower portion 23 and an upper portion 25 opposite the first lower portion 21 and the second lower portion 23. The first lower portion 21 and the second lower portion 23 are preferably separably formed, wherein each lower portion preferably receives a respective leg of a medical instrument 12. The recessed portion 27 is formed between the first lower portion 21 and the second lower portion 23 as shown in FIGS. 1 through 5. The recessed portion 27 is preferably positioned upon a respective tool rack 14 (i.e. pliers rack) when storing or sterilizing the medical instrument 12 (i.e. surgical pliers) within the pouch 20 as illustrated in FIG. 1. Sterilizing the surgical pliers or other hinged instruments 12 upon the pliers rack 14 prevents the pouches 20 from being stacked upon one another, wherein stacking multiple medical instruments 12 upon one another may prevent the sterilization substance from coming in contact with the entire medical instrument 12. Utilizing the tool rack 14 allows the pouches 20 to be spaced adequately apart and thus allows the sterilization substance to effectively contact all surfaces of the medical instrument 12.

Figure 16:
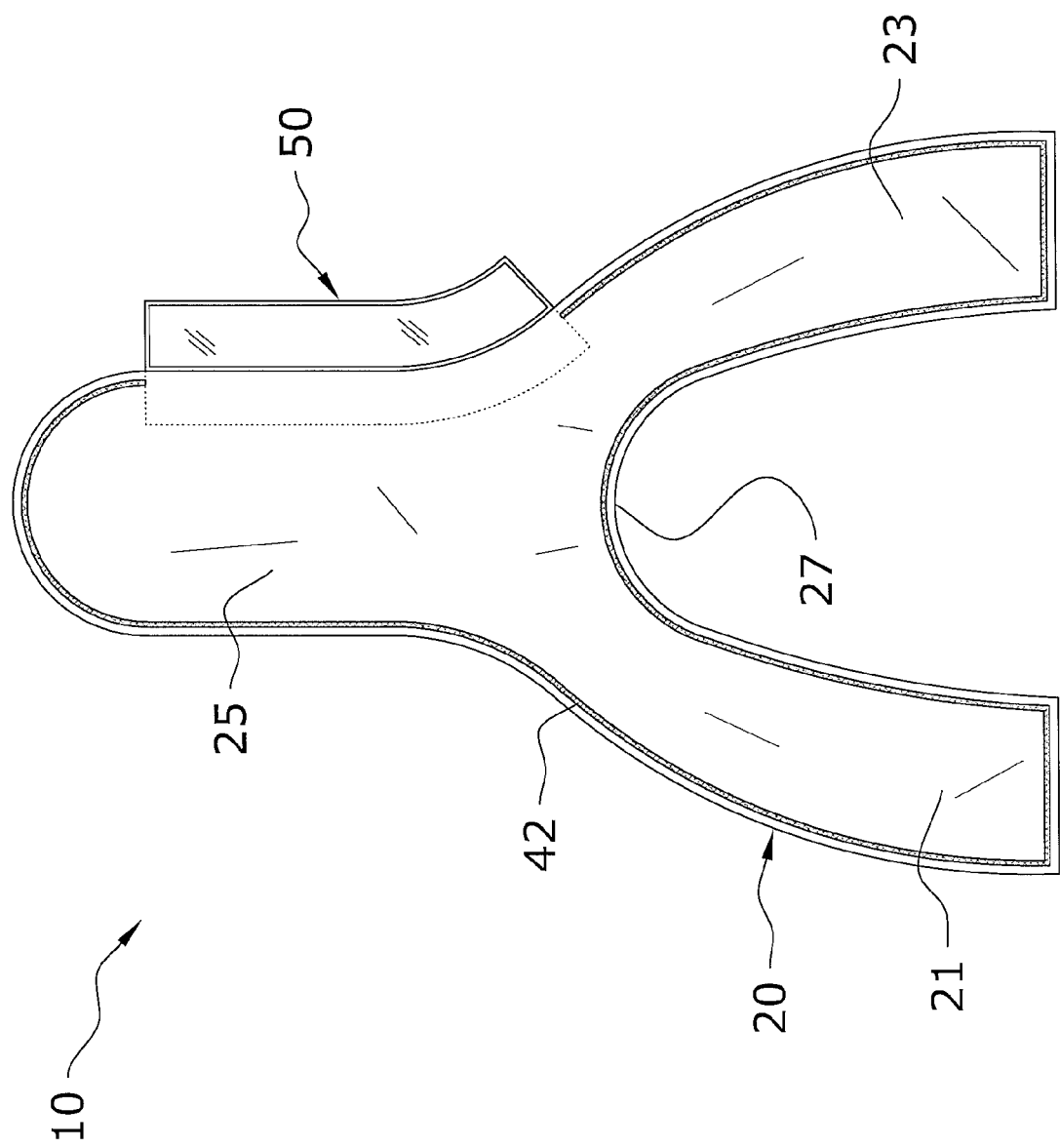
FIG. 16 is a front view of a sixth alternative embodiment of the present invention.
Figure 17:
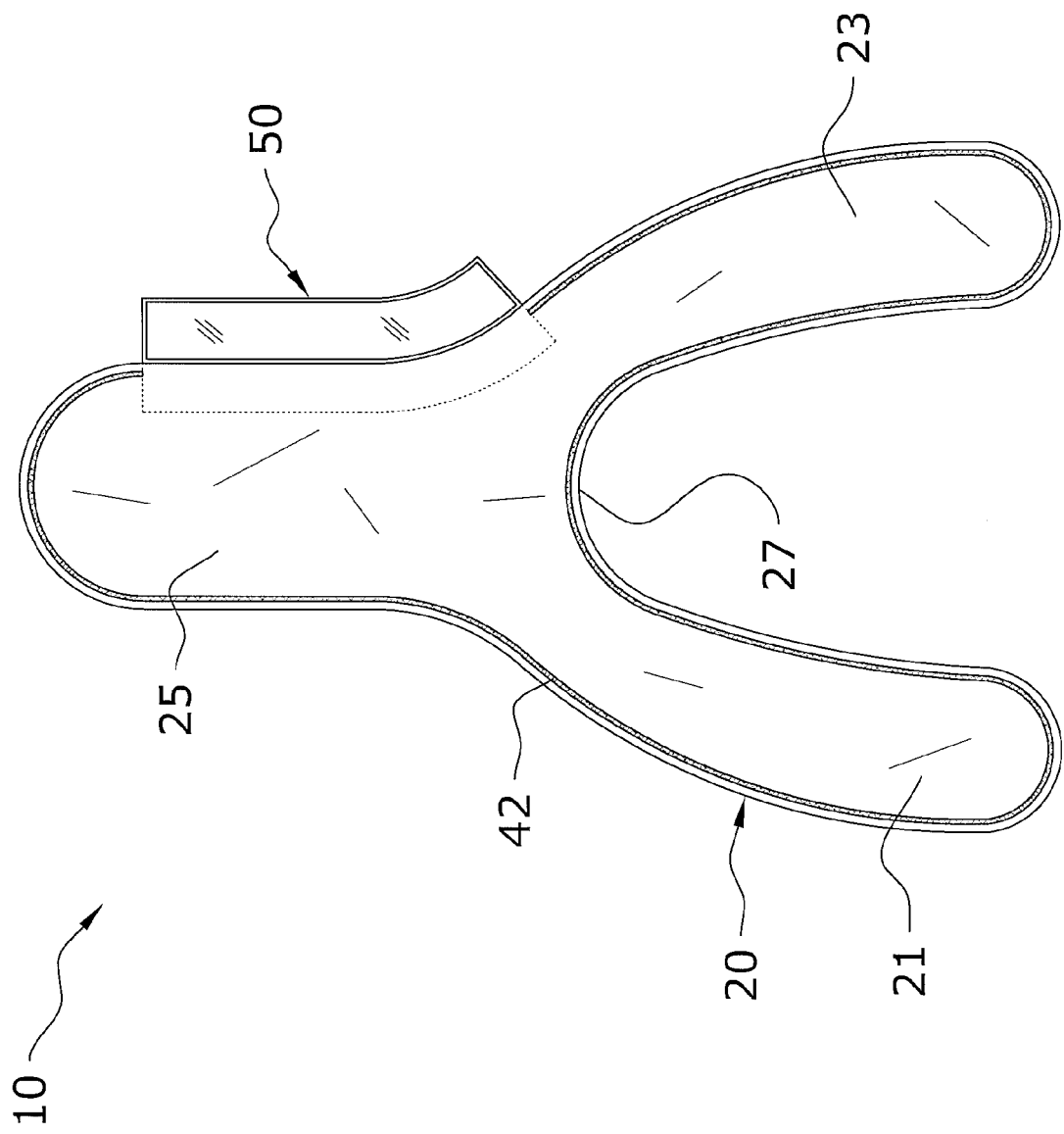
FIG. 17 is a front view of a seventh alternative embodiment of the present invention.

The recessed portion 27 is preferably comprised of a triangular shaped configuration. An apex of the recessed portion 27 preferably extends upwardly toward the upper portion 25 as shown in FIGS. 1 through 5. It is appreciated that the recessed portion 27 may also be comprised of a substantially semi-circular or oval shaped configuration as illustrated in FIGS. 16 and 17. It is further appreciated that the recessed portion 27 may be comprised of a plurality of various configurations all which substantially separate the first lower portion 21 from the second lower portion 23 as illustrated in FIGS. 11 through 15.

Figure 2:
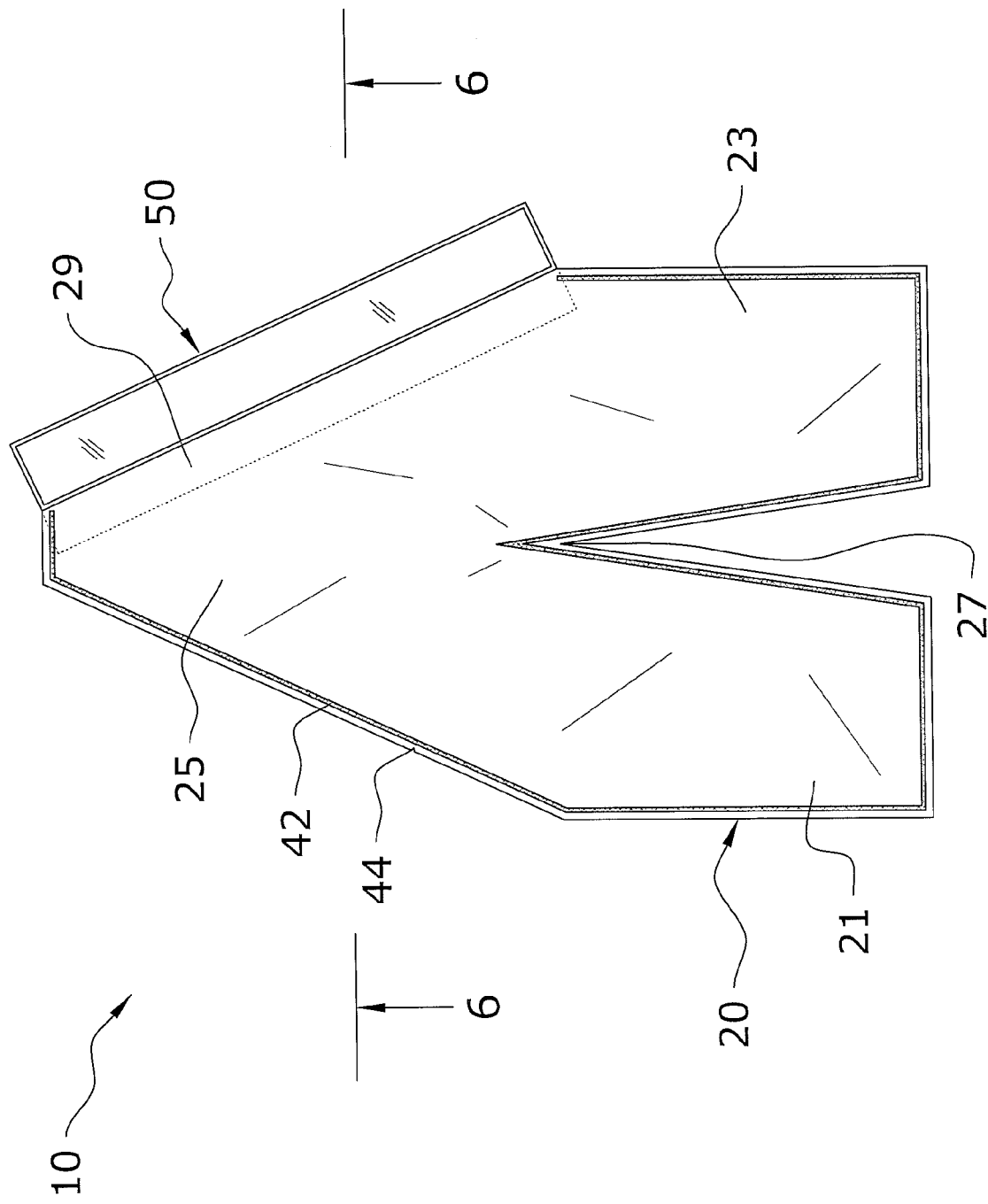
FIG. 2 is a front view of the present invention.
Figure 3:
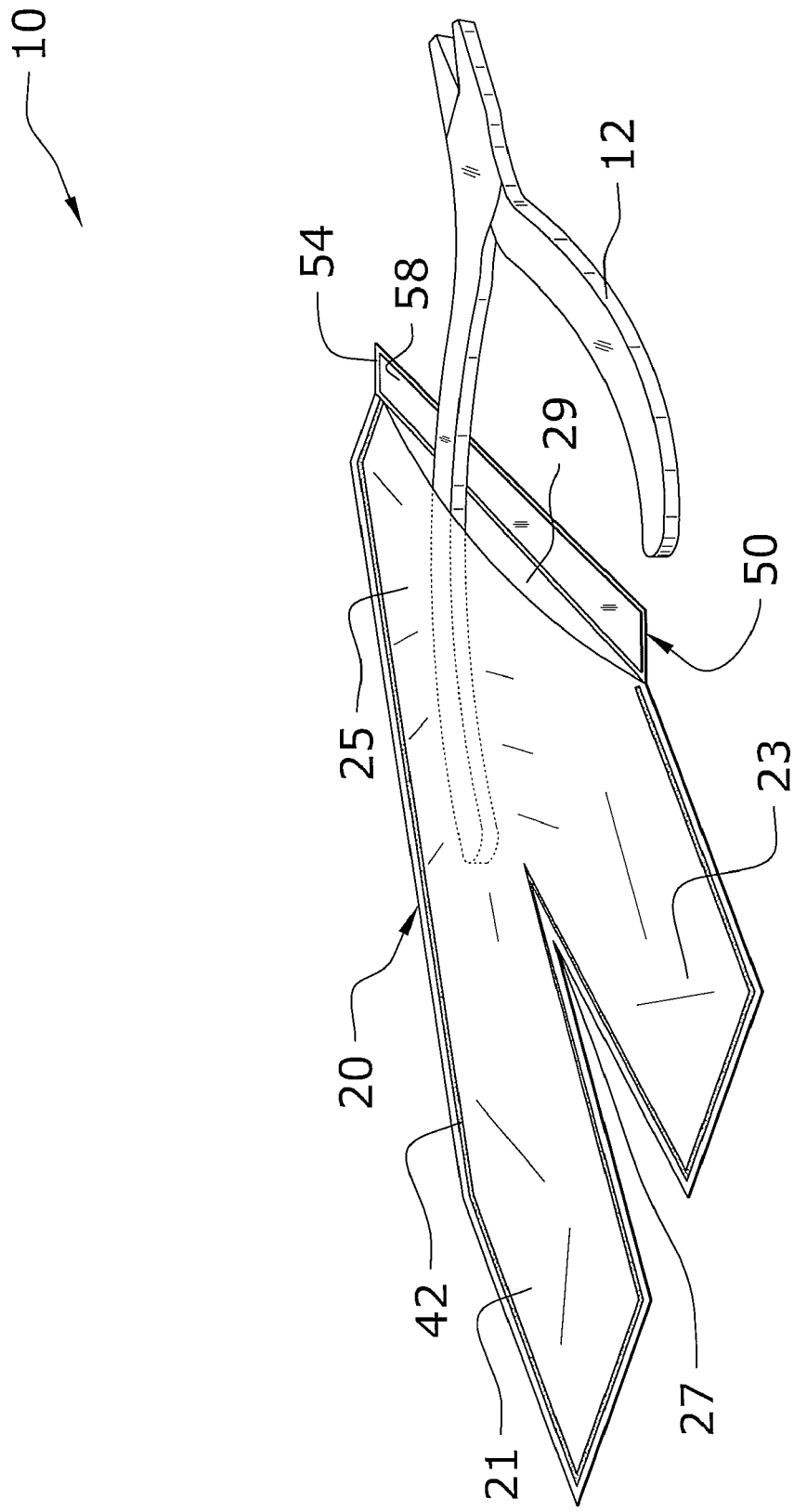
FIG. 3 is an upper perspective view of the present invention with a medical instrument partially inserted within the pouch.

The first lower portion 21 and the second lower portion 23 preferably substantially mirror each other as shown in FIG. 2. The ends of the first lower portion 21 and the second lower portion 23 may also be comprised of a plurality of configurations, such as but not limited to flat, inclined or rounded as illustrated in FIGS. 2 and 11 through 17.

Figure 4:
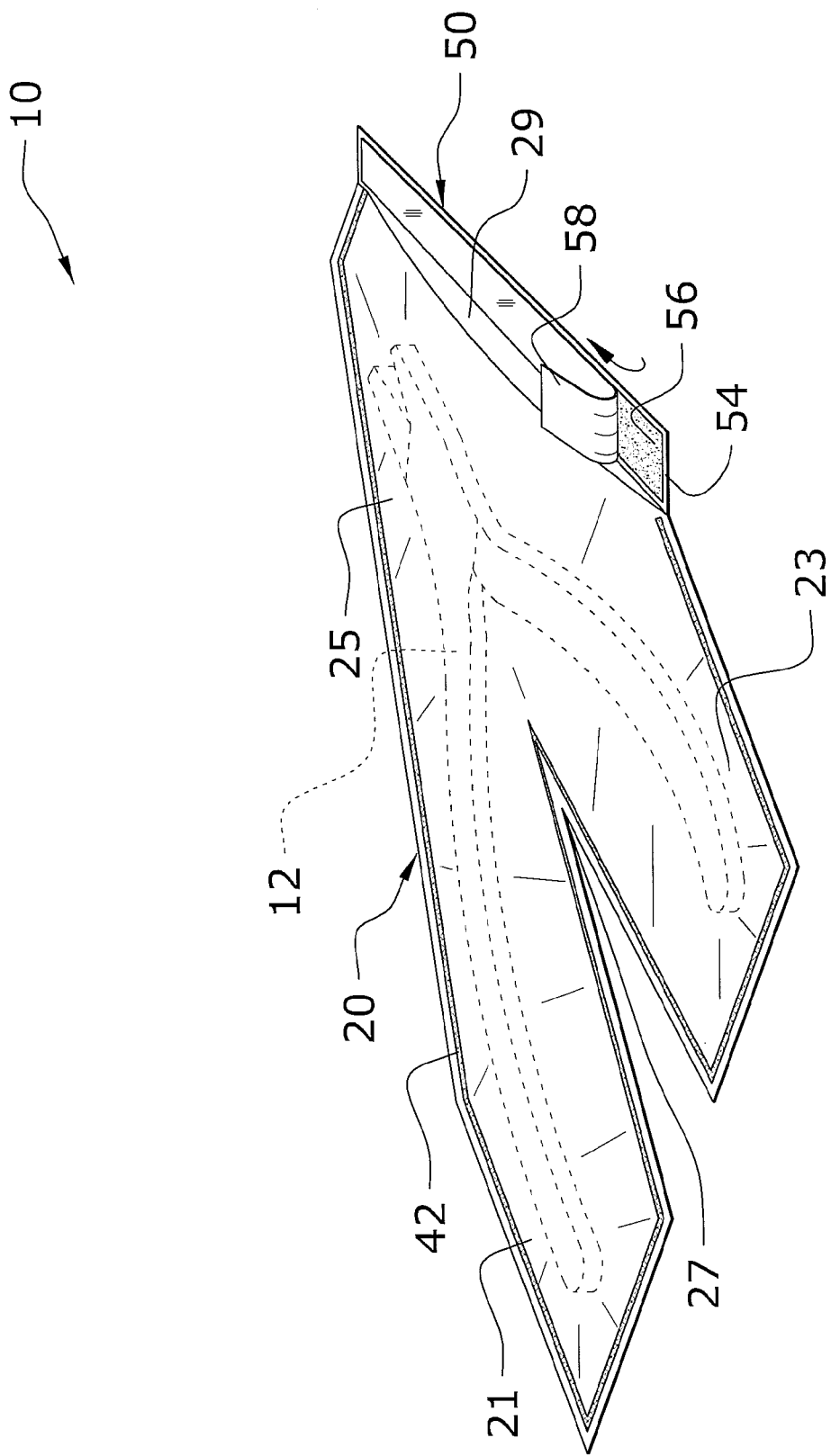
FIG. 4 is an upper perspective view of the present invention with a medical instrument inserted within the pouch.
Figure 5:
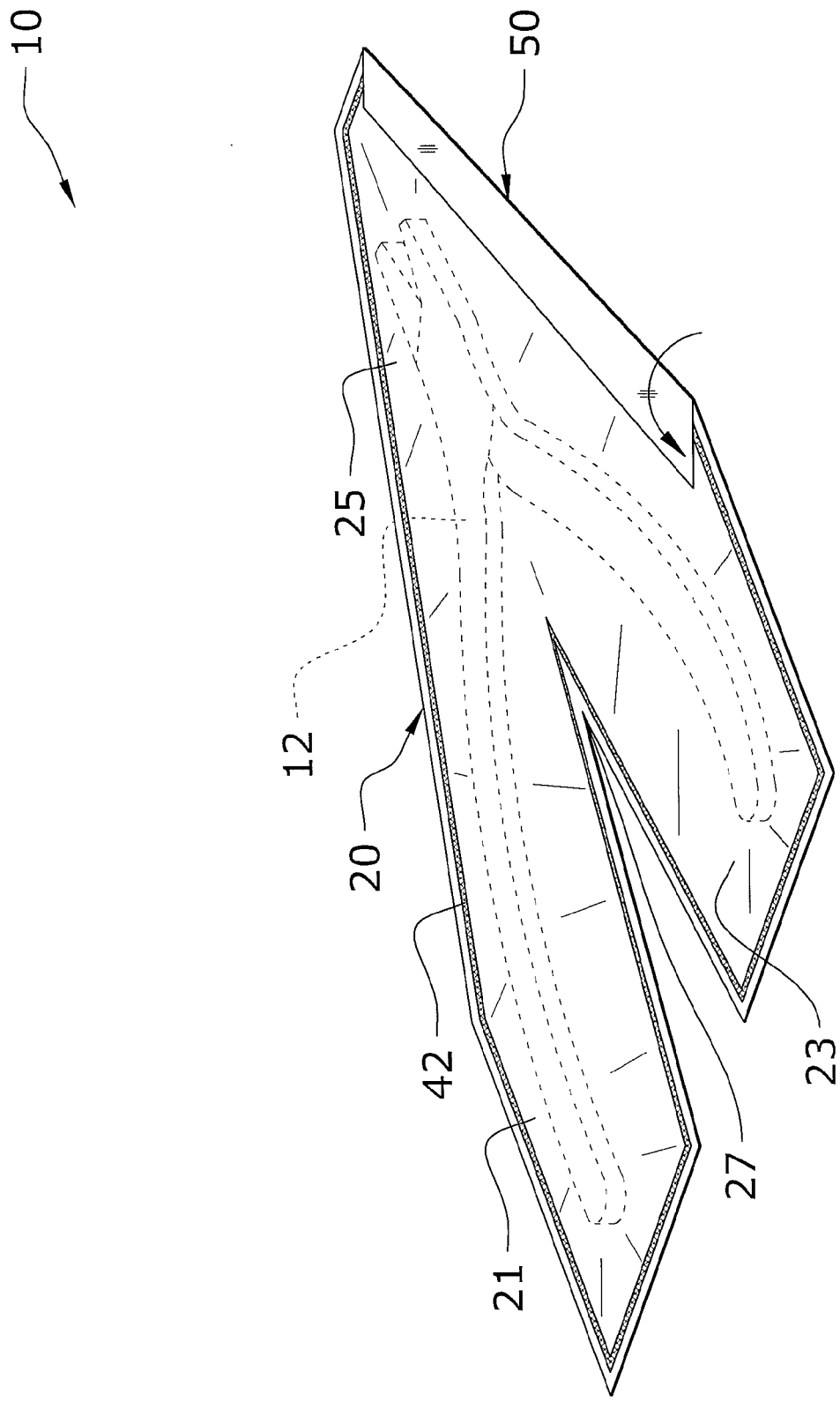
FIG. 5 is an upper perspective view of the present invention with a medical instrument inserted within the pouch and the flap sealed upon the pouch.

The upper portion 25 extends upwardly from lower portions 21, 23 and preferably receives the head of the medical instruments 12 as illustrated in FIGS. 1, 4 and 5. The upper portion 25 may also be comprised of a plurality of configurations, as illustrated in FIGS. 11 through 17. The upper portion 25 may include at least one tapered edge or a bottle neck configuration to better conform to the overall shape of the medical instrument 12 as illustrated in FIG. 2. The inside of the pouch 20 is preferably fluidly connected from the first lower portion 21 to the upper portion 25 to the second lower portion 23. The inside of the first lower portion 21 is preferably substantially fluidly sealed from the inside of the second lower portion 23 via the recessed portion 27.

The opening 29 is preferably formed along at least one edge of the upper portion 25 of the pouch 20 as shown in FIGS. 1 through 5, wherein the outer seal 42 does not extend across the perimeter of the first layer 30 and the second layer 40 along the opening 29. The opening 29 is further preferably positioned along a tapered end of the upper portion 25 as illustrated in FIGS. 1 through 5. The opening 29 allows access to the inside of the pouch 20 between the first layer 30 and the second layer 40. The opening 29 is also preferably large enough to allow the hinged instrument to be inserted adequately into the pouch 20.

C. Flap

The flap 50 covers the opening 29 after the medical instrument 12 has been inserted within the pouch 20 to prevent contaminants and toxins from coming into contact with the medical instrument 12. The flap 50 preferably extends along an entire length of the opening 29 as shown in FIGS. 1 through 5. The flap 50 is further preferably parallel with the opening 29.

The flap 50 includes a first flange portion 52 and a second flange portion 54. The first flange portion 52 is preferably attached to the upper portion 25 and is substantially parallel with the opening 29. The second flange portion 54 preferably extends outwardly from the first flange portion 52 as shown in FIG. 6. The second flange portion 54 further preferably extends outwardly from the upper portion 25. The second flange portion 54 is also preferably parallel with the opening 29 as illustrated in FIG. 6.

The second flange portion 54 preferably includes a sealing member 56 extending across a longitudinal axis of the second flange portion 54 as shown in FIG. 4. The sealing member 56 is positioned about an upper side of the second flange portion 54 of the flap 50. The sealing member 56 is further preferably comprised of an adhesive material so as to adequately stick to the upper side of the first layer 30. An outer layer 58 is preferably removably attached to the upper side of the sealing member 56 to prevent foreign substances from attaching to the sealing member 56 when not in use.

The sealing member 56 and the outer layer 58 function in a similar manner to a sticker, wherein the backing of the sticker must be removed to attach the sticky surface to an object. It is appreciated that the opening 29 of the pouch 20 may be sealed utilizing a plurality of various manners rather than the preferred method, such as but not limited to a self-sealing extremity or a thermo-sealing blade.

D. Manufacture of Invention

Figure 7:
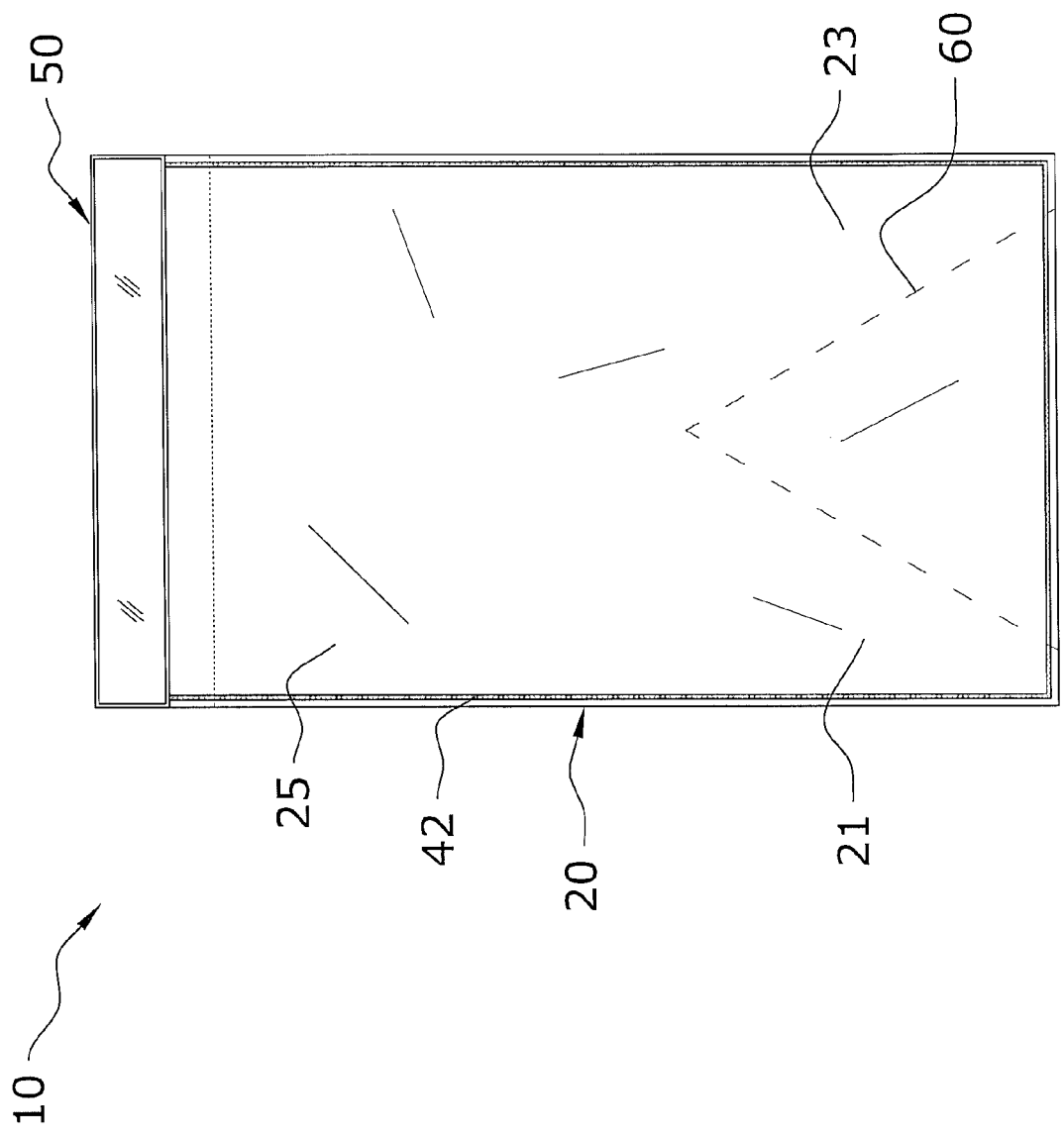
FIG. 7 is a front view of a pouch illustrating a first step in a first example of manufacturing the present invention.
Figure 8:
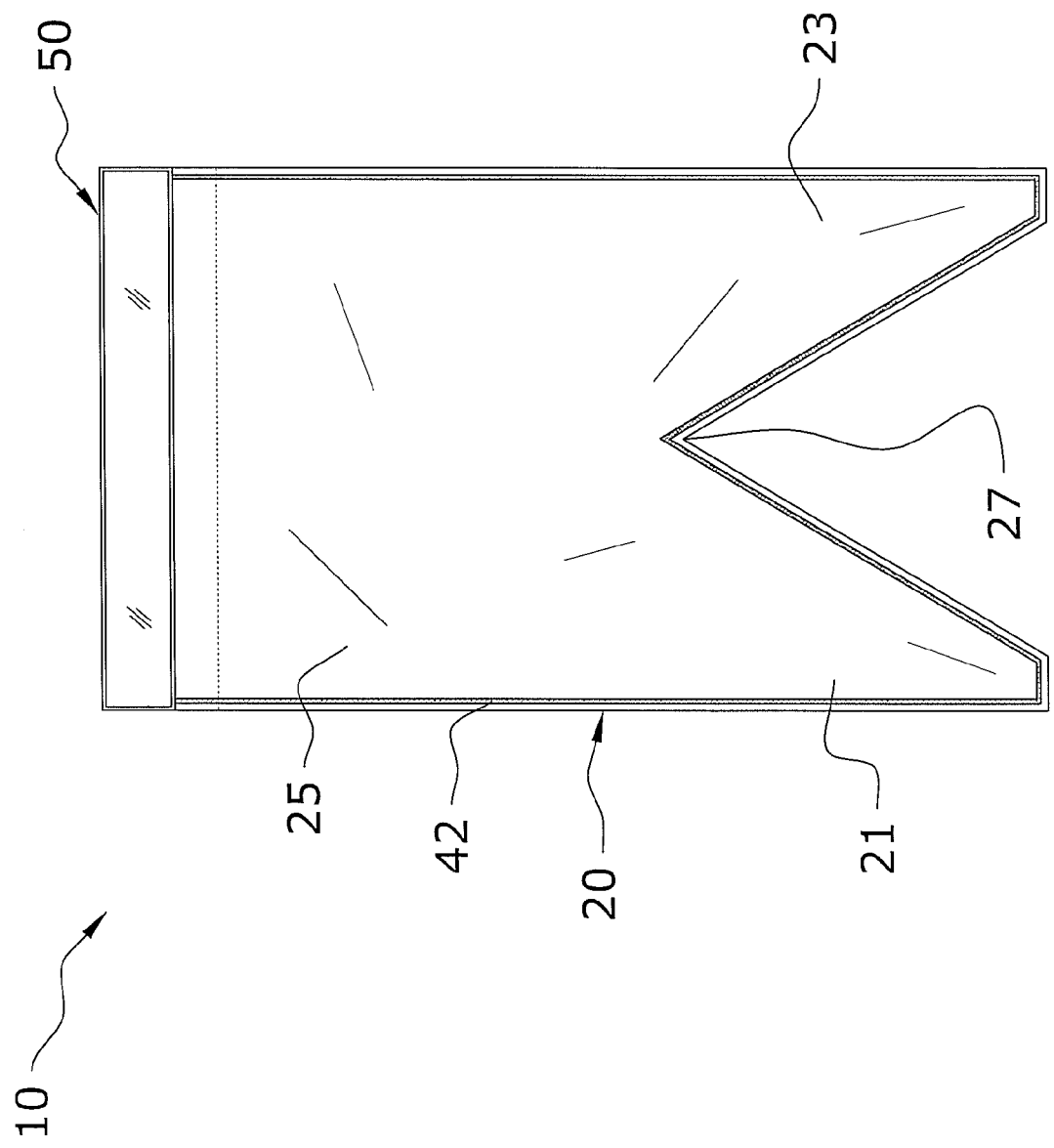
FIG. 8 is a front view of a pouch illustrating a second step in the first example of manufacturing the present invention.

The present invention may be manufactured in various manners as illustrated in FIGS. 7 through 11. A first example of a way to manufacture the present invention involves utilizing a standard rectangular pouch 20 as illustrated in FIGS. 7 and 8. A wedge is cut out of the pouch 20 from a substantially center bottom edge of the pouch 20 as illustrated by the cutting line 60 in FIG. 7. The wedge is preferably comprised of a substantially triangular shaped configuration. The wedge is then removed from the bottom of the pouch 20, thus forming a first lower portion 21, a second lower portion 23 and a recessed portion 27 between thereof. The perimeter of the recessed portion 27 is then sealed to prevent any microorganisms or toxins from entering the inside of the pouch 20 via the recessed portion 27.

Figure 9:
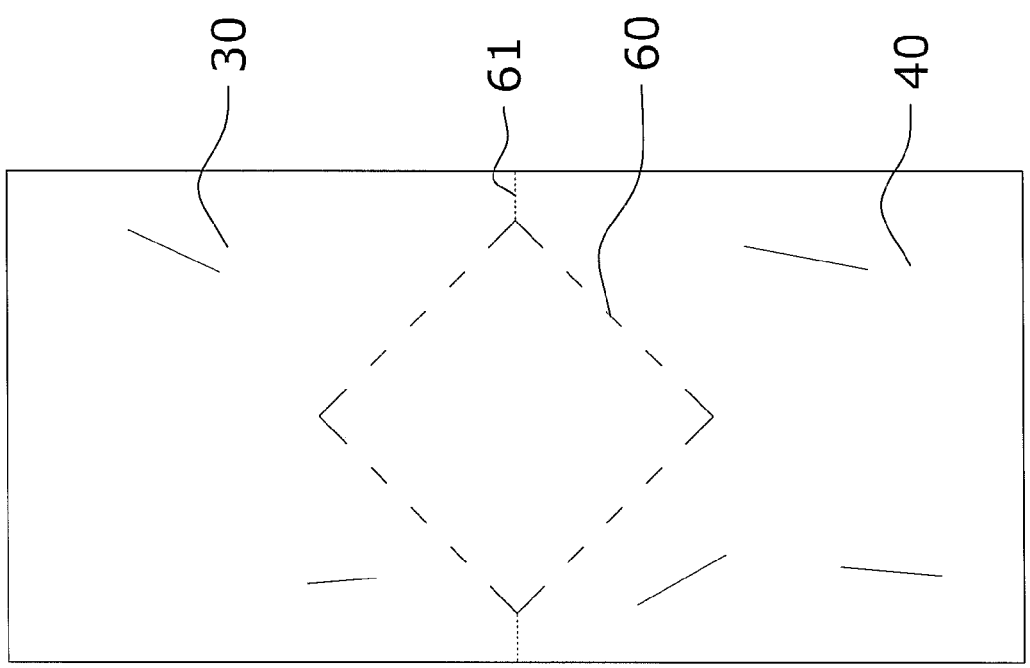
FIG. 9 is a front view of a pouch illustrating a first step in a second example of manufacturing the present invention.
Figure 10:
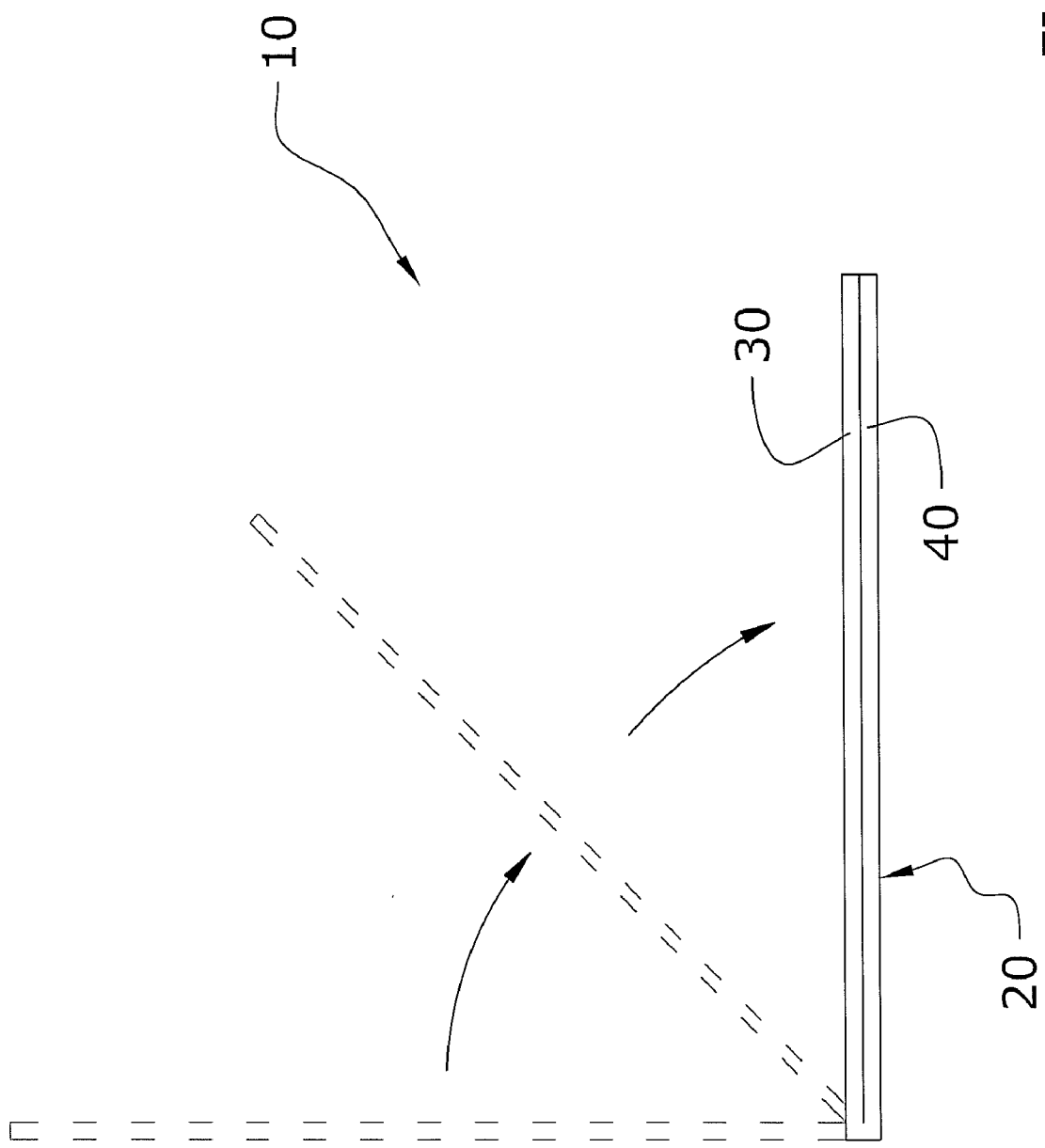
FIG. 10 is a front view of a pouch illustrating a second step in the second example of manufacturing the present invention.
Figure 11:
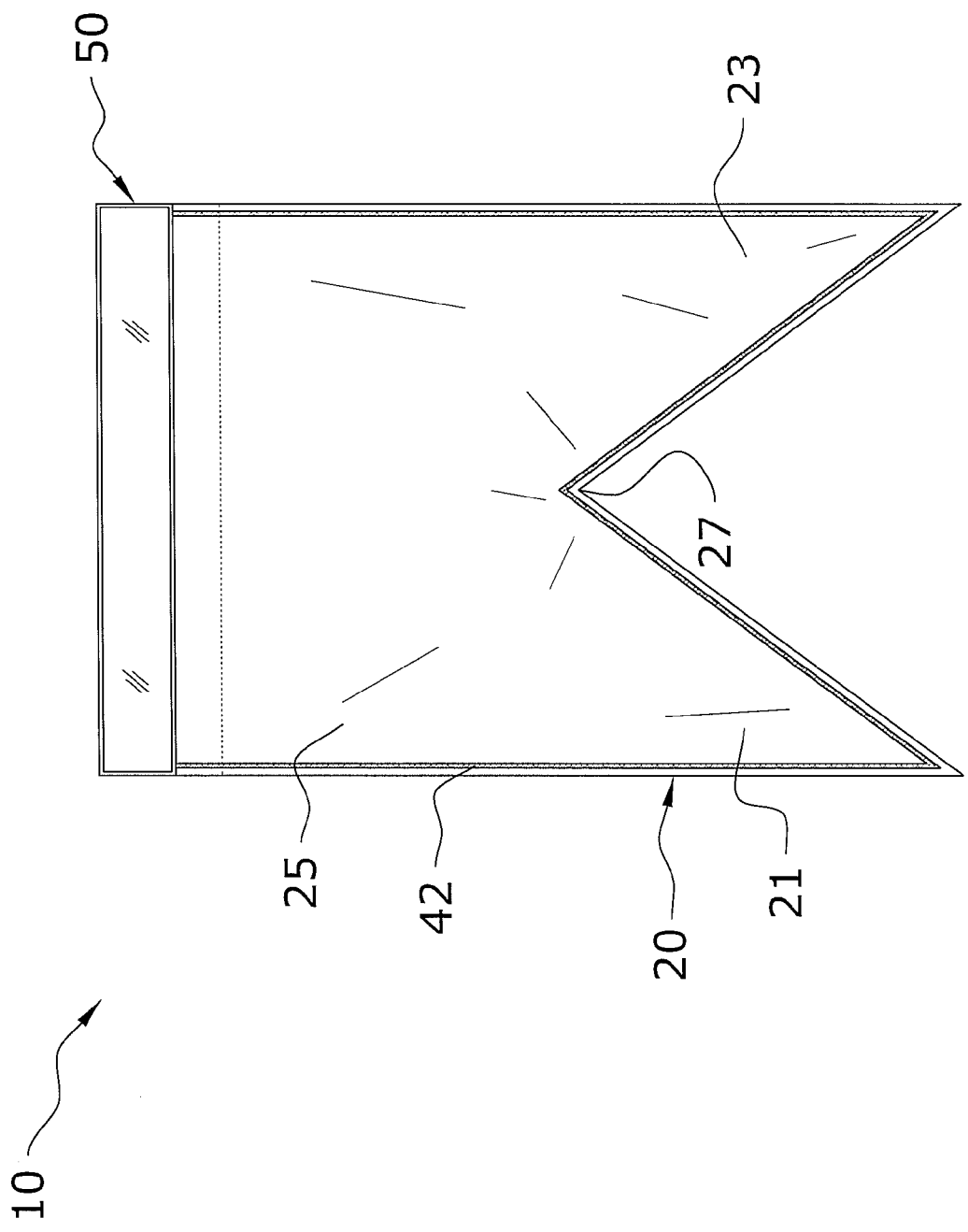
FIG. 11 is a front view of a first alternative embodiment of the present invention.
Figure 12:
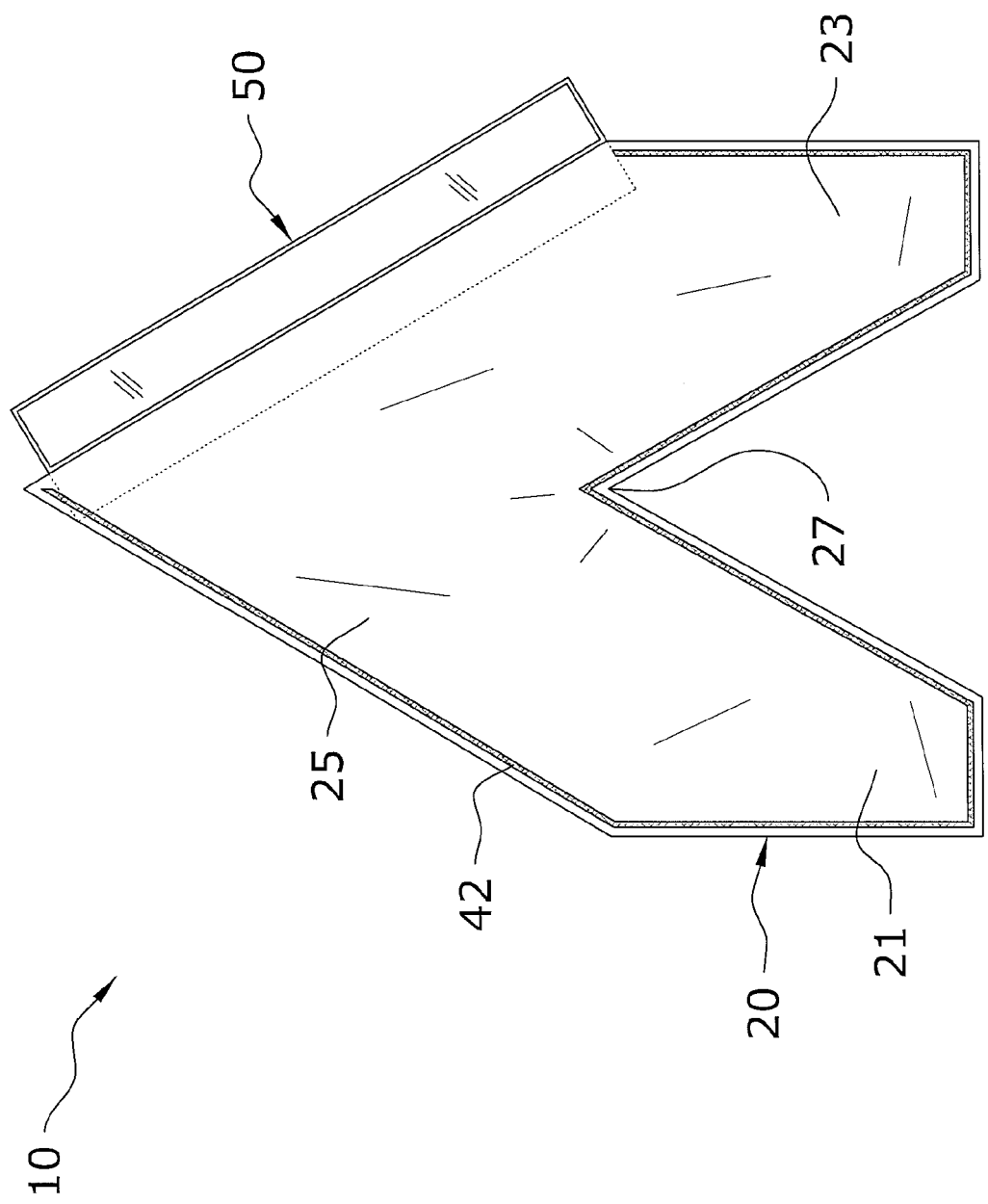
FIG. 12 is a front view of a second alternative embodiment of the present invention.
Figure 13:
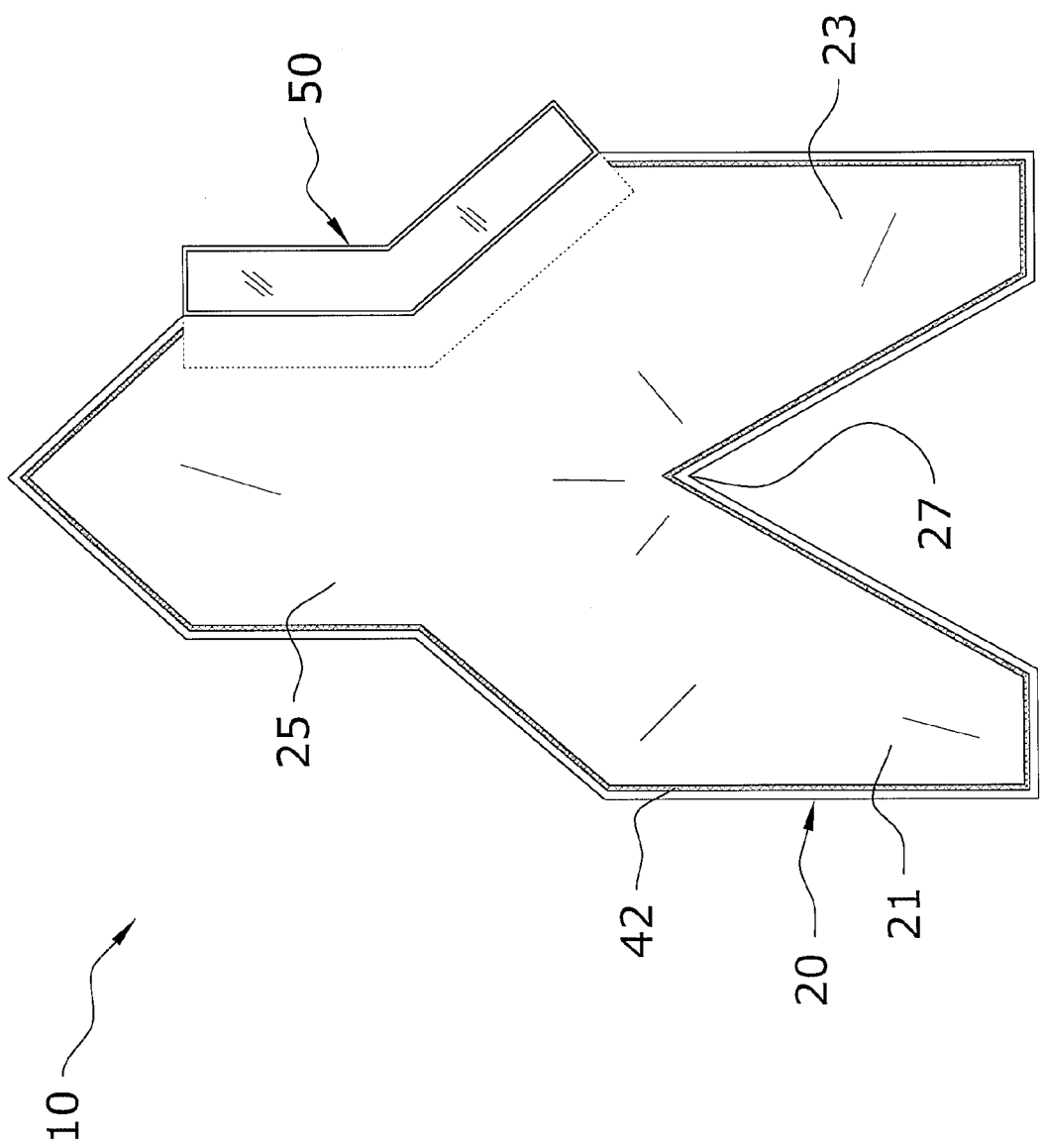
FIG. 13 is a front view of a third alternative embodiment of the present invention.
Figure 14:
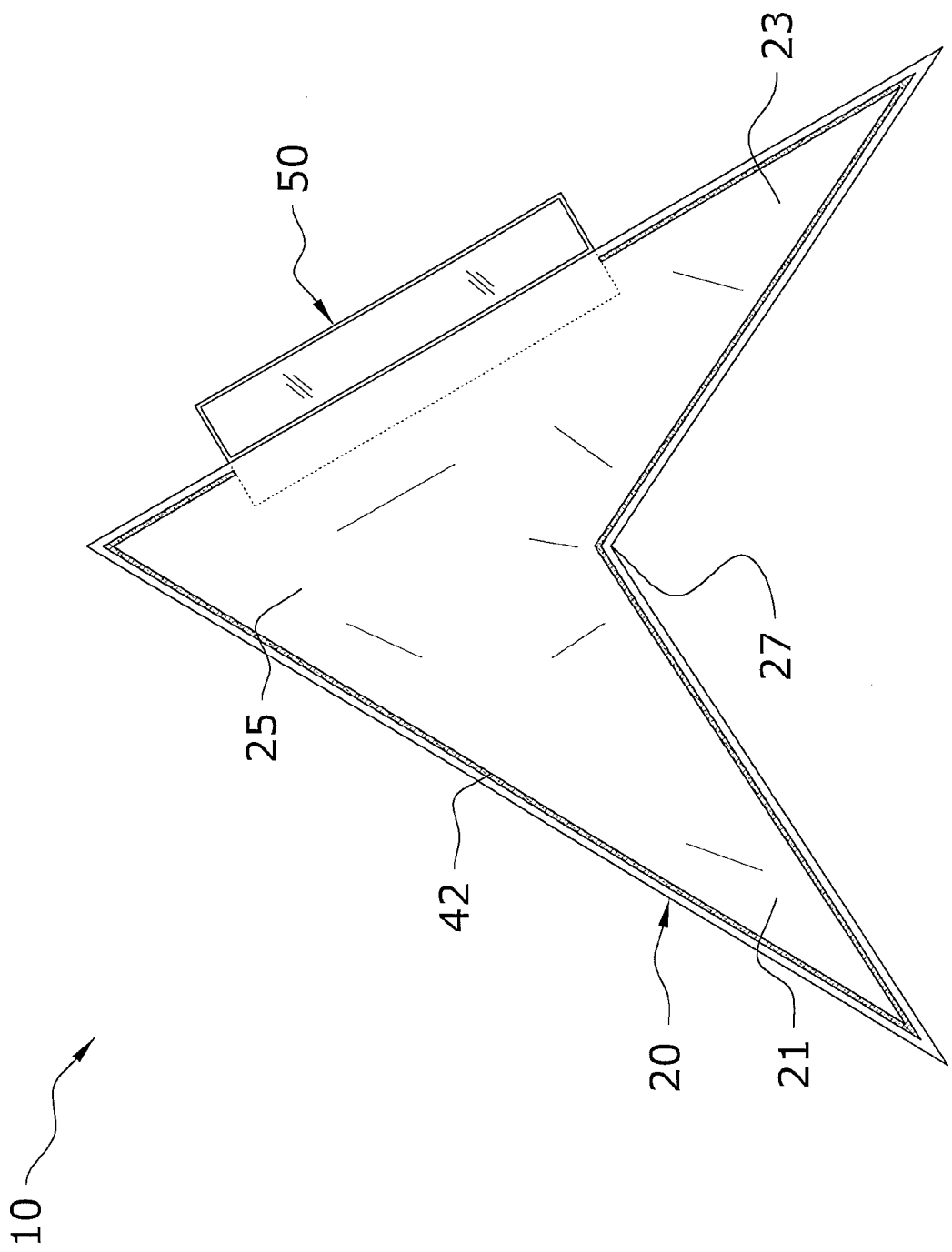
FIG. 14 is a front view of a fourth alternative embodiment of the present invention.
Figure 15:
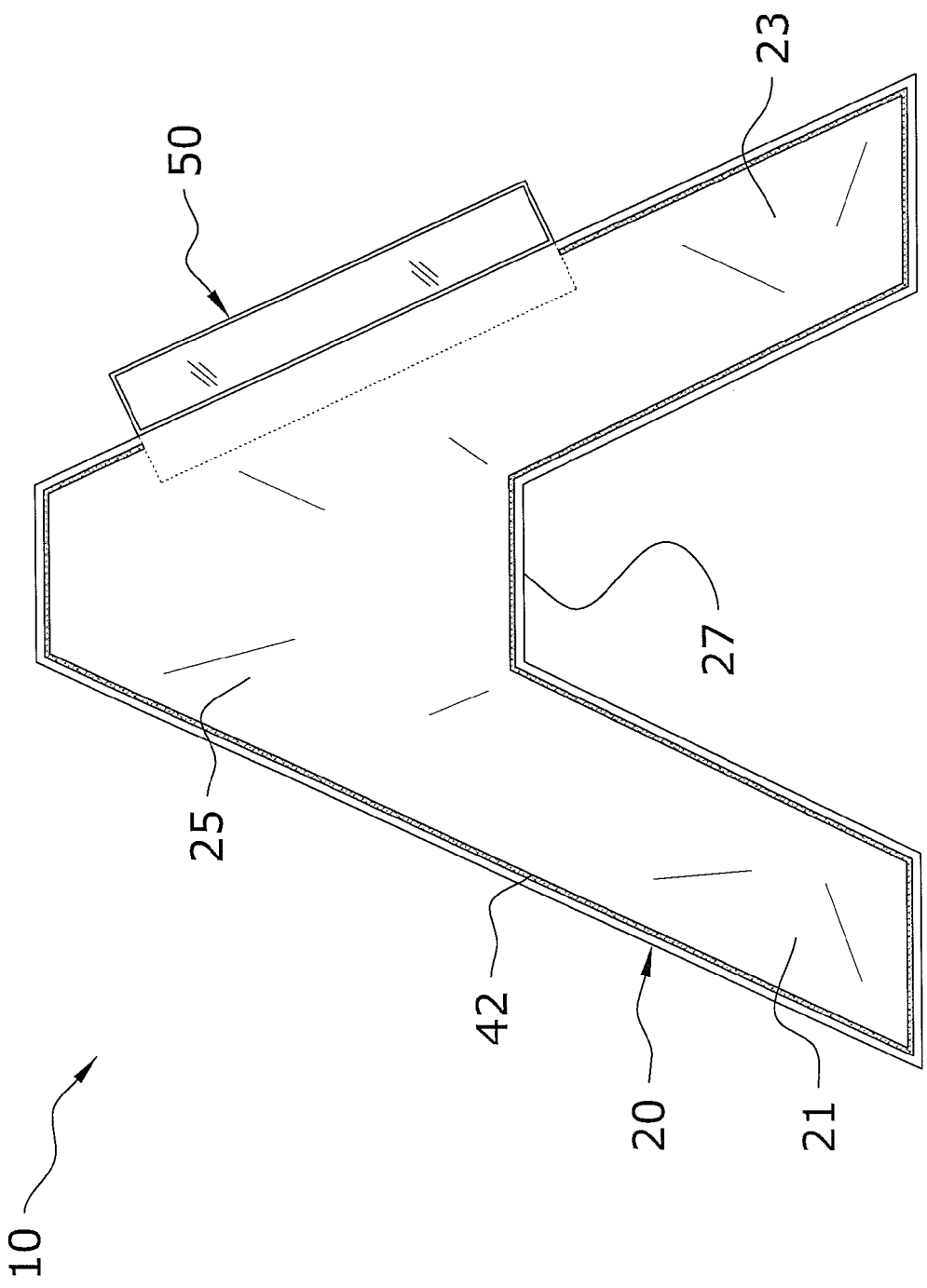
FIG. 15 is a front view of a fifth alternative embodiment of the present invention.

A second example of a way to manufacture the present invention is illustrated in FIGS. 9 and 10. A quadrilateral shaped hole is first cut through a substantial center of the sheet as illustrated by the cutting line 60 in FIG. 9. The sheet is preferably comprised of a pouch 20 material. The quadrilateral shaped hole is preferably cut, wherein each opposing corner perpendicularly faces an outer edge of the sheet as illustrated in FIG. 9. The quadrilateral shaped hole is then removed from the sheet, thus forming a hole in the center of the sheet. The sheet is then folded in the middle as illustrated by the folding line 61 in FIG. 9. The opposing ends of the sheet are thus joined and form a pouch 20 as shown in FIG. 10. The pouch 20 may then be sealed around the outer perimeter of the pouch 20. An opening 29 is also preferably left unsealed to allow insertion of a medical instrument 12. It is appreciated that the present invention may be manufactured in a plurality of manners other than the described manners above.

E. In Use

In use, the medical instrument 12 (i.e. surgical pliers) is first inserted within the pouch 20 by inserting the handles or legs of the medical instrument 12. Each respective leg is inserted within the respective lower portion 21, 23 of the pouch 20 and the head of the medical instrument 12 is inserted within the upper portion 25 of the pouch 20. When the medical instrument 12 is adequately positioned within the sealed pouch 20 the medical instrument 12 may be sterilized via various techniques, such as but not limited to steam sterilization. It is appreciated that the medical instrument 12 may be sterilized in a plurality of manners and also before insertion into the pouch 20.

The outer layer 58 of the flap 50 is then removed thus revealing the sealing member 56. The second flange portion 54 is then folded over the opening 29 of the pouch 20 and the sealing member 56 is attached to the upper surface of the first layer 30 thus sealing the medical instrument 12 within the pouch 20. The medical instrument 12 may now be positioned upon the respective tool rack 14 (i.e. pliers rack). When the user is ready to utilize the medical instrument 12 the above process is simply reversed. The sealed pouch 20 can also be opened by utilizing a scissors to cut open the pouch 20. In addition, a slit 44 anywhere along the non-sealed periphery of the pouch 20, as shown in FIG. 2, would allow the operator to tear open the pouch 20 with their fingers.

What has been described and illustrated herein is a preferred embodiment of the invention along with some of its variations. The terms, descriptions and figures used herein are set forth by way of illustration only and are not meant as limitations. Those skilled in the art will recognize that many variations are possible within the spirit and scope of the invention, which is intended to be defined by the following claims (and their equivalents) in which all terms are meant in their broadest reasonable sense unless otherwise indicated. Any headings utilized within the description are for convenience only and have no legal or limiting effect.

I claim:

1. A pliers and pliers sterilization pouch, comprising:
   a hinged pliers, said pliers having a working head, a first leg, and a second leg, each of said legs extending from said working head in a hinged manner; and
   a pouch having an inner space to extend within an upper portion, a first lower portion, and a second lower portion of said pouch, said upper portion receives said working head, said first lower portion receives said first leg, and said second lower portion receives said second leg;
   wherein said first lower portion is separated from said second lower portion via a recessed portion extending between said first lower portion and said second lower portion, said recessed portion formed and separated from said inner space via an outer seal substantially surrounding an outer perimeter of said pouch and wherein said upper portion is connected via said inner space to said first lower portion and said second lower portion;
   wherein said pouch includes a first layer and a second layer, wherein said first layer and/or said second layer are comprised of a gas permeable material, wherein said first layer is attached to said second layer via said outer seal and wherein said first layer and said second layer form said inner space between thereof;
   wherein said first layer and said second layer are comprised of substantially similar configurations, wherein said first layer and said second layer are separably formed substantially along at least one outer edge thus forming an opening, said opening adapted to receive said hinged pliers within said inner space of said pouch, wherein said at least one outer edge is along said upper portion, and wherein said upper portion is above said recessed portion.

2. The pliers and pliers sterilization pouch of claim 1, including a flap foldably connected to said first layer or said second layer along said upper portion, said flap adapted to cover said opening.

3. The pliers and pliers sterilization pouch of claim 2, wherein said flap includes a first flange portion and a second flange portion, said first flange portion being attached to said upper portion and substantially parallel to said opening, said second flange portion extending outwardly from said first flange portion and from said upper portion, said second flange portion being parallel to said opening and said second flange portion including a sealing member extending across a longitudinal axis of said second flange portion, said sealing member positioned about an upper side of the second flange portion, said sealing member having an adhesive material thereon to adhere to said pouch.

4. The pliers and pliers sterilization pouch of claim 1, wherein said upper portion is above said recessed portion and wherein said upper portion is comprised of a triangular shape.

5. The pliers and pliers sterilization pouch of claim 1, wherein said upper portion is above said recessed portion and wherein said upper portion is comprised of a rectangular shape.

6. A process for making a medical instrument sterilization pouch, comprising:
   supplying a sterilization pouch including an opening, wherein said sterilization pouch is comprised of a rectangular shaped configuration;
   removing a triangular shaped section from a first end of said sterilization pouch, wherein said first end is opposite said opening; and
   sealing an outer perimeter of said sterilization pouch formed from removing said triangular shaped section.

* * * * *